United States Patent
Shi et al.

(10) Patent No.: US 10,188,357 B2
(45) Date of Patent: Jan. 29, 2019

(54) SUPPORT UNIT, SUPPORT DEVICE, AND EMISSION TOMOGRAPHY DEVICE USING SUPPORT DEVICE

(71) Applicant: DONGGUAN SONGSHAN LAKE SOUTHERN MEDICAL UNIVERSITY SCI. & TECH. PARK CO., LTD., Dongguan (CN)

(72) Inventors: Han Shi, Beijing (CN); Jianfeng Xu, Wuhan (CN); Qiyu Peng, Wuhan (CN)

(73) Assignee: DONGGUAN SONGSHAN LAKE SOUTHERN MEDICAL UNIVERSITY SCI. & TECH. PARK CO., LTD., Guangdong (CN)

( * ) Notice: Subject to any disclaimer, the term of this patent is extended or adjusted under 35 U.S.C. 154(b) by 0 days.

(21) Appl. No.: 15/525,947

(22) PCT Filed: Nov. 6, 2015

(86) PCT No.: PCT/CN2015/093966
§ 371 (c)(1),
(2) Date: May 10, 2017

(87) PCT Pub. No.: WO2016/074590
PCT Pub. Date: May 19, 2016

(65) Prior Publication Data
US 2017/0303871 A1     Oct. 26, 2017

(30) Foreign Application Priority Data
Nov. 11, 2014  (CN) .......................... 2014 1 0631706

(51) Int. Cl.
*G01T 1/20*    (2006.01)
*A61B 6/03*    (2006.01)
*A61B 6/00*    (2006.01)

(52) U.S. Cl.
CPC ............... *A61B 6/037* (2013.01); *A61B 6/44* (2013.01); *A61B 6/42* (2013.01)

(58) Field of Classification Search
CPC ..... G01T 1/2914; G01T 1/1644; G01T 1/2985; A61B 6/037; A61B 6/4233
See application file for complete search history.

(56) References Cited

U.S. PATENT DOCUMENTS 4,075,527 A * 2/1978 Cummings ............... H01J 1/88
156/295
4,209,700 A  6/1980 Stoddart
(Continued)

FOREIGN PATENT DOCUMENTS

CN  1643619 A  7/2005
CN  1886674 A  12/2006
(Continued)

OTHER PUBLICATIONS

International Search Report for International Application No. PCT/CN2015/093966 dated Feb. 2, 2016.

*Primary Examiner* — Kenneth J Malkowski
(74) *Attorney, Agent, or Firm* — Wolf, Greenfield & Sacks, P.C.

(57) ABSTRACT

A support unit (200), a support device (100) and an emission tomography device using the support device (100) are provided. The support unit (200) comprises: a support body (210), in which an accommodation space (220) that penetrates through the support body is provided, comprising multiple support positions (230A, 230B) that are distributed along a circumferential direction of the accommodation space (220); and multiple fastening means (240A, 240B), connected to at least some of the multiple support positions. At least some of the multiple fastening means (240A, 240B) can move between a contraction position and an extension position along a radial direction of the accommodation space (220). The fastening means (240A, 240B) are used to fasten detectors of the emission tomography device. When the fastening means (240A, 240B) are located at the contraction position, a first detector fastening ring of a first diameter is (Continued)

formed, and when the fastening means (240A, 240B) are located at the extension position, a second detector fastening ring of a second diameter that is smaller than the first diameter is formed. The emission tomography device using the support unit (200) can adjust at least a radial length of a detection chamber, so that a relatively large three-dimensional space angle can be obtained, thereby improving detection sensitivity.

19 Claims, 12 Drawing Sheets

(56) References Cited

U.S. PATENT DOCUMENTS

| | | |
|---|---|---|
| 2004/0097800 A1 | 5/2004 | Crosetto |
| 2007/0007454 A1 | 1/2007 | Stoddart et al. |
| 2008/0230704 A1 | 9/2008 | Daghighian |
| 2009/0242778 A1* | 10/2009 | Ukita .............. G01T 1/249 250/370.09 |
| 2011/0024636 A1* | 2/2011 | Gagnon .............. G01T 1/2985 250/362 |

FOREIGN PATENT DOCUMENTS

| | | |
|---|---|---|
| CN | 1919147 A | 2/2007 |
| CN | 101120876 A | 2/2008 |
| CN | 101990643 A | 3/2011 |
| CN | 102283664 A | 12/2011 |
| CN | 102871731 A | 1/2013 |
| CN | 103479372 A | 1/2014 |
| CN | 103479378 A | 1/2014 |
| CN | 104473657 A | 4/2015 |
| CN | 105342632 A | 2/2016 |
| JP | H09-313475 A | 12/1997 |
| JP | H11-211833 A | 8/1999 |

* cited by examiner

300A

300B

700

700

700

700

SUPPORT UNIT, SUPPORT DEVICE, AND EMISSION TOMOGRAPHY DEVICE USING SUPPORT DEVICE

This application is a national stage filing under 35 U.S.C. § 371 of International Application No. PCT/CN2015/093966, filed on Nov. 6, 2015, which claims priority to Chinese Application No. CN 201410631706.8, filed on Nov. 11, 2014, the contents of each of which are incorporated herein by reference in their entireties.

TECHNICAL FIELD

The present invention relates to medical apparatus and instruments, more specifically, to a support unit of the emission tomography device, a support device comprising the support unit and an emission tomography device comprising the support device.

BACKGROUND

Emission tomography technology such as PET (Positron Emission Tomography) and SPECT (Single-Photon Emission Computed Tomography) has been extensively used in many fields such as medical diagnosis, pathology and pharmacology research, drug development and the like.

For example, the PET uses the annihilation effect which occurs between the positron produced by isotope decay and negatron within human body, to obtain the distribution information of the isotope within human body through injecting radioactive tracer into human body (e.g., compounds with positron isotope labeling) and detecting gamma photons generated from the annihilation effect by the detector. The reconstruction of the distribution information could be carried out with a computer to get the three-dimensional tomographic image of the labeled compound distribution within the human body.

One of the most important parameters of the medical emission tomography system (e.g., whole-body PET system) is the detection sensitivity, which represents the ability of the system acquiring effective signal data, and is critical to the spatial resolution of the image reconstructed by the system. Clinically, the relatively high detection sensitivity contributes to the reduction of the dosage of the radioactive tracer, the shortening of the imaging time and the improvement of the SNR (Signal to Noise Ratio). The detection sensitivity of the emission tomography system depends on the geometrical efficiency and the detection efficiency to the inherent coincidence event. The geometrical efficiency depends on the space angle surrounded by the detector modules.

Currently, the emission tomography system still adopts a traditional design scheme. That is, each of the detector modules has substantially the same performance and size, and the detector modules are permanently fixed after the emission tomography system is built, which restricts the detection sensitivity in some cases. For example, the detection sensitivity would decrease when the emission tomography system suitable for the whole human body is applied to a child or a small animal.

SUMMARY

To solve the problem of a narrow application scope of the emission tomography device in the prior art, the present invention provides a support unit for the emission tomography device, a support device comprising the support unit and an emission tomography device comprising the support device.

In some embodiments, the present invention provides a support unit for an emission tomography device, comprising:

a support body, provided with an accommodation space running through the support body therein, wherein the support body comprises a plurality of support positions that are distributed along a circumferential direction of the accommodation space;

a plurality of fastening means, connected to at least a portion of the plurality of support positions, for fixing detectors of the emission tomography device, wherein at least a portion of the plurality of fastening means are movable between contraction positions and extension positions along radial directions of the accommodation space, wherein the fastening means are used for forming a first detector fastening ring with a first diameter when at the contraction positions and forming a second detector fastening ring with a second diameter which is smaller than the first diameter when at the extension positions.

Preferably, the fastening means are at the contraction positions, the fastening means on a plurality of the support units arranged side by side along the axial direction of the accommodation space are capable of forming the first detector fastening ring together.

Preferably, when the fastening means are at the extension positions, the fastening means on the same support body are capable of forming the second detector fastening ring; or the fastening means on a plurality of the support units arranged side by side along the axial direction of the accommodation space are capable of forming the second detector fastening ring together.

Preferably, the fastening means are spaced apart, such that only one corresponding support position has the fastening means connected thereto for every predetermined number of support positions.

Preferably, the plurality of support positions are configured that when a predetermined number of the support units are arranged side by side along the axial direction of the accommodation space, support positions on different support units are staggered and arranged alternately along the circumferential direction, in order for the fastening means on the predetermined number of the support units to form the first detector fastening ring alternately.

Preferably, the plurality of the support positions are configured that when the predetermined number of the support units are arranged side by side along the axial direction, support positions on different support units are staggered and arranged alternately in the same order.

Preferably, the predetermined number is a composite number, the number of the extension positions is u, wherein u is the number of the prime factors of the composite number except 1, the u extension positions are arranged along the radial directions of the accommodation space and the distances from the u extension positions to the center of the accommodation space are respectively equal to the product of the reciprocal of each of the u prime factors and r, wherein r is the distance from the fastening means at the contraction position to the center of the accommodation space.

Preferably, the predetermined number is $2^n$, wherein n is an integer greater than or equal to 2; and the number of the extension positions is n, and the distance from the n extension positions to the center of the accommodation space are equal to $r/2, r/4, \ldots r/2^n$, respectively.

Preferably, the support body has a rectangular plate-structure.

Preferably, the support body is provided with guide holes, for guiding the support unit to move along the axial direction of the accommodation space.

In some other embodiments, the present invention provides a support device for an emission tomography device, comprising any one of the plurality of support units as described above, wherein the plurality of support units are arranged side by side along the axial direction of the accommodation space, and the accommodation space form an accommodation chamber for accommodating detectors and a detected object Preferably, the support device further comprises a guide means, for moving the plurality of the support units along the axial direction of the accommodation space.

Preferably, the guide means includes a guide rail arranged along the axial direction of the accommodation space and guide holes arranged on the support bodies, and the guide rail passes through the guide holes to guide the support units to move along the guide rail.

Preferably, when the support body has a rectangular plate-structure, the guide means comprises four guide rails and four guide holes arranged at four corners of each of the support bodies.

Preferably, the support device further comprises: an elastic buffer means, arranged between the adjacent support units to apply equivalent elastic force to the support units on two sides of the elastic buffer means; and a positioning device, for positioning the support units in the axial direction of the accommodation space.

In yet other embodiments, the present invention also provides an emission tomography device comprising: any support device as described above; and a detector, fixed to the fastening means within the accommodation chamber.

In the emission tomography device built by the support units provided by the present invention, at least the radial length of its detection chamber is adjustable. Thus, a detection chamber with a relative larger bore diameter could be form as required, for example, for an adult, and a detection chamber with a relative smaller bore diameter could be formed as required, for example, for a child or a small animal. Therefore, a relative larger space angle could be obtained as compared with the emission tomography device in the prior art, and thus the detection sensitivity of the emission tomography device is improved effectively.

A series of simplified concepts are introduced into the present invention and they will be described in more detail in the part of the embodiments. The summary of the present invention does not intend to define the key features and essential technical features of the technical solution to be claimed and determine the protection scope of the technical solution to be claimed.

The advantages and features will be described in detail with reference to the appended drawings.

BRIEF DESCRIPTION OF THE DRAWINGS

The following drawings are provided as part of the present invention and serve to help understanding the present invention. The drawings illustrate embodiments of the present invention and the description thereof and serve to explain the principle of the present invention. In the drawings, FIG. 1 schematically illustrates a support device according to an embodiment of the present invention;

FIG. 2A to FIG. 2B schematically illustrate a support unit according to an embodiment of the present invention in different states respectively, wherein FIG. 2A shows all of the fastening means at contraction positions and FIG. 2B shows a portion of the fastening means at extension positions;

DETAILED DESCRIPTION

The description of the present invention will be provided in great detail below so that it could be understood thoroughly. However, the person skilled in the art could understand that the description below relates to the preferable embodiments of the present invention and the present invention could be implemented without one or more details as described herein. Moreover, some technical features that are well known in the art are not involved in the description in order to avoid the confusion with the present invention.

Once a traditional emission tomography device is built, its sizes in various directions are fixed. The present invention provides a support unit for the emission tomography device and a support device comprising the support unit. The radial length (i.e., bore diameter) of the emission tomography device is adjustable by the support device. Thus, some preferable embodiments could also provide an emission tomography device having adjustable radial and axial length. The above emission tomography device may be, for example, a PET device or a SPECT device. Preferably, the emission tomography device is a PET device. Though adjusting the bore diameter or both the bore diameter and the axial length of the emission tomography device according to the volume of the detected object, such as human and experimental animal, the device has an optimized detection sensitivity.

Figure 1:
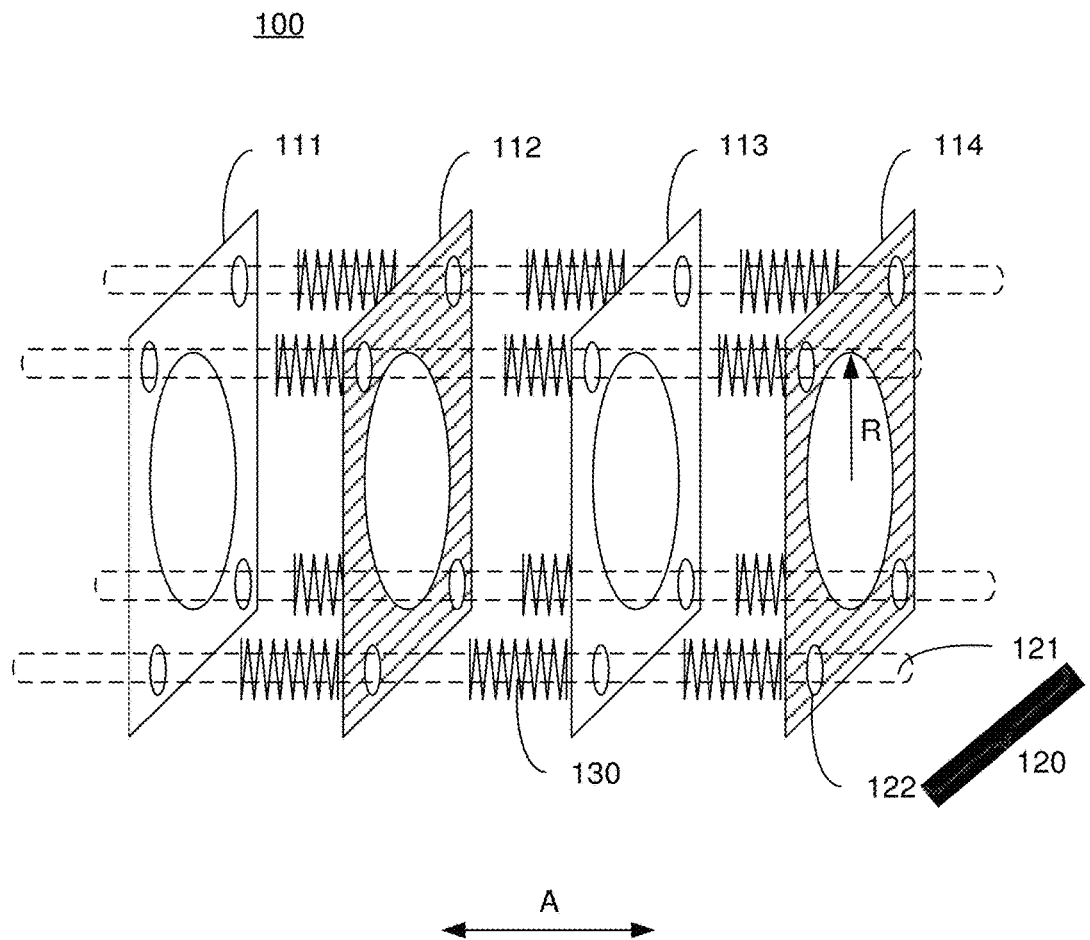

FIG. 1 illustrates a support device according to a preferable embodiment of the present invention. The support device 100 comprises a plurality of support units, such as the support units 111, 112, 113 and 114. These support units 111, 112, 113 and 114 may have the same structure or different structure, which will be described in detail below. It is noted that the quantity of the support unit as shown in the drawing is for illustrative purpose only, aimed at explaining the principle of the present invention. Actually, the quantity of the support units could be determined depending on the axial size of the detected object, the required detection sensitivity and the like.

Figure 2A:
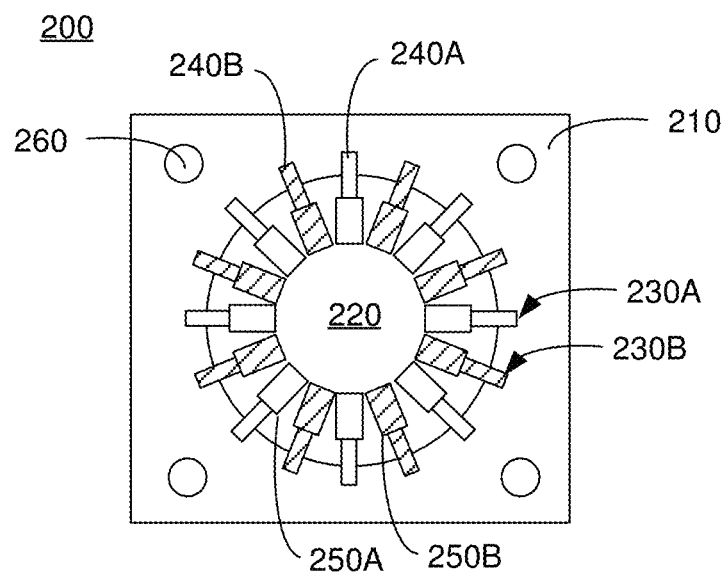
Figure 2B:
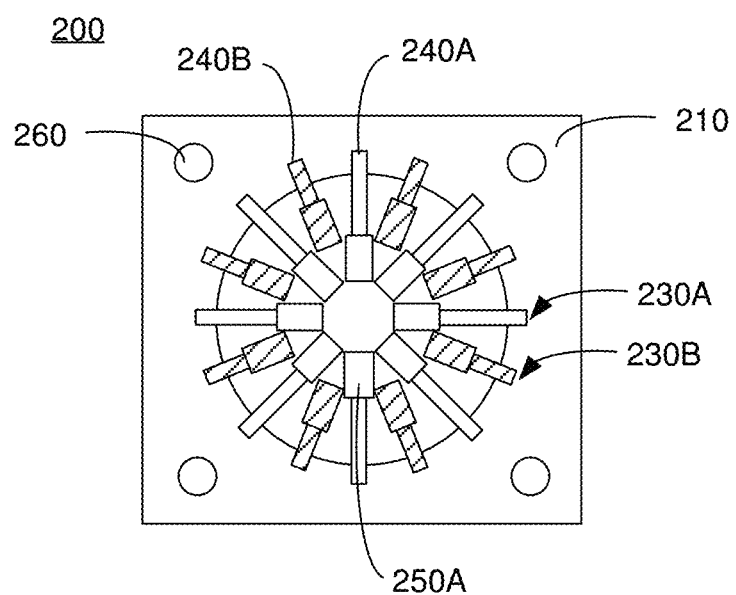

FIG. 2A to FIG. 2B schematically illustrate a support unit according to an embodiment of the present invention in different states respectively, wherein FIG. 2A shows all of the fastening means at contraction positions and FIG. 2B shows a portion of the fastening means at extension positions. As illustrated in FIG. 2A to FIG. 2B, the support unit 200 comprises a support body 210 and fastening means 240.

Within the support body 210, there is an accommodation space 220 passing through it. The support body 210 may be made of the metal material, such as aluminum, steel and stainless steel, the plastic material having enough strength, and the like. The cross section of the support body 210 is not limited to the rectangle as shown in FIG. 2A to FIG. 2B. The cross section may also be in shape of a circle, an oval, a triangle, a pentagon, a hexagon, a heptagon and the like, or even in an irregular shape, as long as an accommodation space 220 meeting the requirement that will be discussed below could be formed within the support body 210. The accommodation space 220 serves as an accommodating chamber for accommodating the detectors and the detected object, as will be explained hereinafter. The accommodation space 220 may have the shape of a cylinder, a cuboid (or a cube), a polygon prism, elliptic cylinder, or any other shape, as long as the accommodation space 220 could form the accommodating chamber mentioned above when a plurality of support units are arranged along the axial direction side by side. The principle of the present invention is merely described with reference to the embodiments having a cylinder-shaped accommodation space 220 in the drawings.

It is noted that, the direction terms "axial direction", "radial direction" and "circumferential direction" are all defined relative to the accommodation space. To be specific, the "axial direction" refers to the direction along which the accommodation space passes through the support body, for example, the direction indicated by the arrow A as shown in FIG. 1. The "radial direction" refers to the direction perpendicular to the axial direction that extends through the center of the accommodation space across the cross section of the accommodation space, for example, the direction indicated by the arrow R as shown in FIG. 1. The "circumferential direction" refers to the direction perpendicular to the axial direction that surrounds the accommodation space in the cross section.

In addition, the support body 210 comprises a plurality of support positions, for example 230A and 230B, arranged along the circumferential direction of the accommodation space 220. These support positions 230A and 230B are used to fix the fastening means 240 in position. For example, the support positions 230A and 230B are respectively connected with the fastening means 240A and 240B. In the embodiments to be described below, it is possible that only a portion of the support positions are used for connecting with the fastening means.

The fastening means 240A and 240B are movably connected to at least a portion of the plurality of support positions 230A and 230B between the contraction positions (as shown in FIG. 2A) and the extension positions (as shown in FIG. 2B) along the radial direction of the accommodation space 220. Preferably, the fastening means 240A and 240B are detachably connected at the support positions. Obviously, the fastening means 240A and 240B may also connected at the support positions in an undetachable manner. In one embodiment, the locations on the support body 210 corresponding to the support positions may be provided with grooves with their openings facing to the center of the accommodation space. The fastening means 240 are movably connected to the grooves along the directions of the openings of the grooves. When the fastening means 240 are needed to be fixed at the contraction positions and the extension positions, an assistant fastener, for example, fastening bolt and the like, could be adopted. In another embodiment, the grooves are replaced with slide tracks extending along the radial direction, such that the fastening means 240A and 240B are connected movably along the slide track. It is undesirable to limit the specific movable connection between the fastening means 240A and 240B and the support body 210 in the present invention. Thus, in addition to the connection mentioned above, other kinds of movable connection known in the art or occurring in the future are all available.

The fastening means 240A and 240B are used to fix the detectors of the emission tomography device. In this embodiment, the detectors are divided into two groups. The two groups of the detectors and their corresponding two groups of fastening means are illustrated by the graphic symbols with and without shadow, respectively. The group of the detectors and the fastening means without shadow are denoted with 250A and 240A respectively, and the group of the detectors and the fastening means with shadow are denoted with 250B and 240B. In order to facilitate the description, the support positions are also divided into two groups in this embodiment. The support positions corresponding to the detectors 250A are denoted with 230A, and the support positions corresponding to the detectors 250B are denoted with 230B. It is noted that, there is no substantial difference between the groups of the detectors, and the dividing herein is just for purpose of facilitating the description to the movement of the fastening means below.

When the fastening means 240A and 240B are all located at their contraction positions, as shown in FIG. 2A, they form a first detector fastening ring with a first diameter. The detectors 250A and 250B on the first detector fastening ring form a detection ring with a relatively larger bore diameter. When a plurality of support units are arranged along the axial direction side by side as shown in FIG. 1, they could form a detection chamber (a chamber surrounded by the detectors) with a larger bore diameter. The detected object (e.g., an adult) with larger volume could enter into the detection chamber for data collection.

When the fastening means 240A (or 240B) are located at the extension positions, as shown in FIG. 2B, the fastening means 240A form a second detector fastening ring with a second diameter which is smaller than the first diameter. The detectors 250A on the second detector fastening ring form a detection ring with a relatively smaller bore diameter. When a plurality of support units are arranged along the axial direction side by side as shown in FIG. 1, they could form a detection chamber with a smaller bore diameter. The detected object with smaller volume (e.g., a child or a small animal) could enter into the detection chamber for data collection.

In this embodiment, since only half of the fastening means move into the extension positions, the number of the detectors on the detection ring at this moment is decreased by half. Therefore, the bore diameter of this detection ring is about half of the bore diameter of the detection ring when the fastening means are all located at contraction positions. In this case, the number of the support positions and the fastening means is preferably even. As for the embodiment illustrated in the drawing, it is possible to merely movably connect one group of the fastening means 240A to the support positions 230A for simplifying the structure of the support units. Similarly, it is also possible to only connect the group of the fastening means 240B to the support positions 230B. Obviously, it is also possible that both the group of the fastening means 240A and 240B are connected to the support positions 230A and 230B.

In order to further reduce the bore diameter of the obtainable detection ring, the support positions and the fastening means may also be divided into three, four or more groups. When the bore diameter of the detection ring needs to be decreased, the fastening means at corresponding positions in each group could move to the extension positions. For example, when both the support positions and the fastening means are divided into three groups, the first, second, or third fastening means of each group along the clockwise direction (or the anticlockwise direction) move to the extension position so as to form a detection ring of a smaller bore diameter. That is, one fastening means is operated every three fastening means. Thus, a detection ring with one third of the initial bore diameter could be formed. Herein and below, the initial bore diameter refers to the bore diameter of the detection chamber or the detection ring when all the fastening means are located at the contraction positions. By analogy, when the support positions and the fastening means are both divided into four groups, a detection ring with one fourth of the initial bore diameter could be obtained; when the support positions and the fastening means are both divided into five groups, a detection ring with one fifth of the initial bore diameter could be obtained; . . . .

It can be seen from the embodiment illustrated in FIG. 2A to FIG. 2B, when a portion of the fastening means, e.g., the fastening means 240A, are located at the extension positions to form the second detector fastening ring with a smaller bore diameter, the detectors on the fastening means 240B are blocked from collecting optical signals, which causes the waste of the detectors. In order to solve this problem, some preferable embodiments are provided below. FIG. 3A to FIG. 3H illustrate a support unit according to a preferable group of embodiments of the present invention in different states respectively, wherein FIG. 3A to FIG. 3D show the fastening means at contraction positions and FIG. 3E to FIG. 3H show the fastening means at extension positions.

Figure 3A:
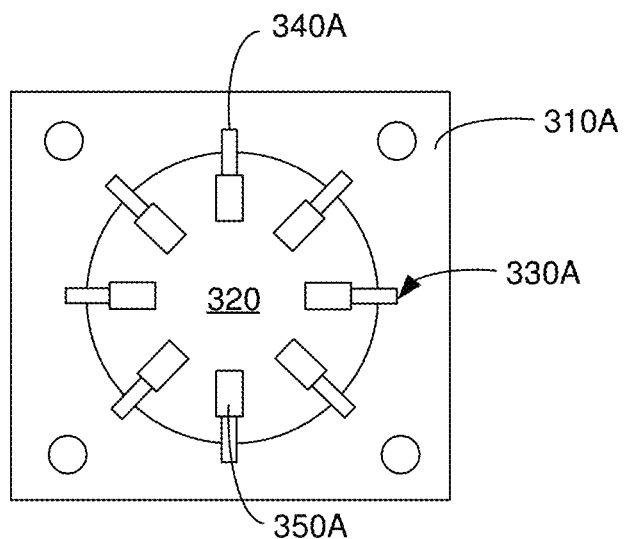
FIG. 3A to FIG. 3B schematically illustrate a support unit according to another embodiment of the present invention, wherein the fastening means are at contraction positions.
Figure 3B:
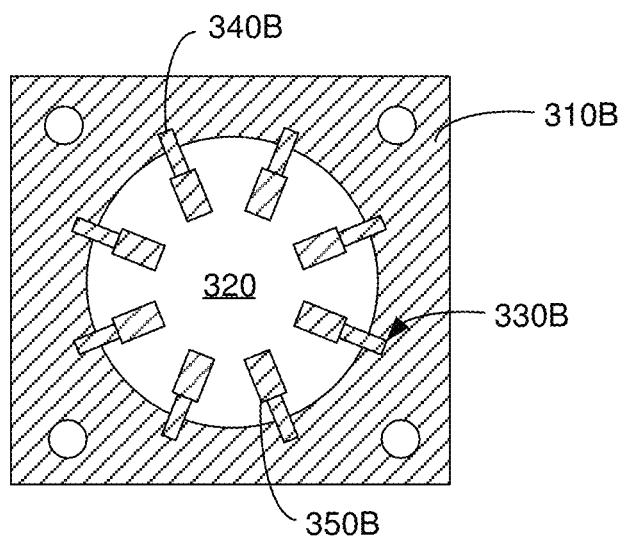
Figure 3C:
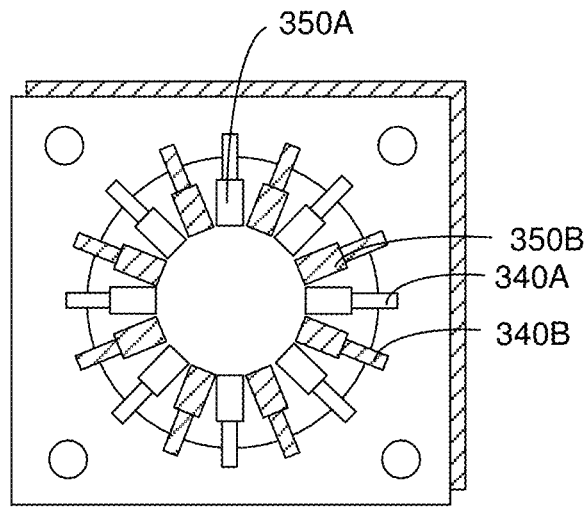
FIG. 3C to FIG. 3D are the front view and the side view of the assembled support units shown in FIG. 3A to FIG. 3B respectively, wherein the fastening means are located at contraction positions.
Figure 3D:
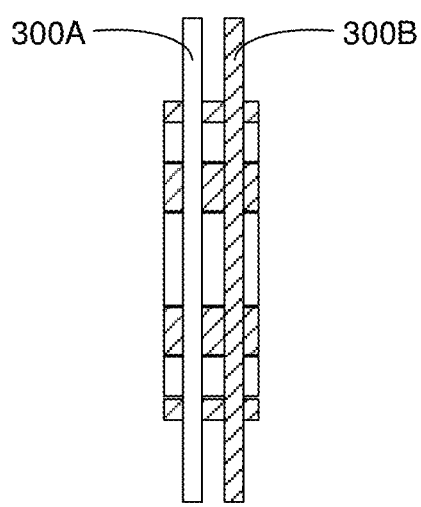
Figure 3E:
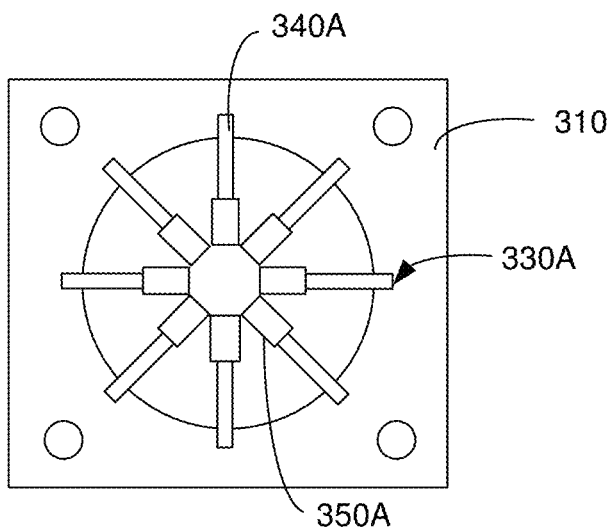
FIG. 3E to FIG. 3F schematically illustrate the support units shown in FIG. 3A to FIG. 3B respectively, wherein the fastening means are located at extension positions.
Figure 3F:
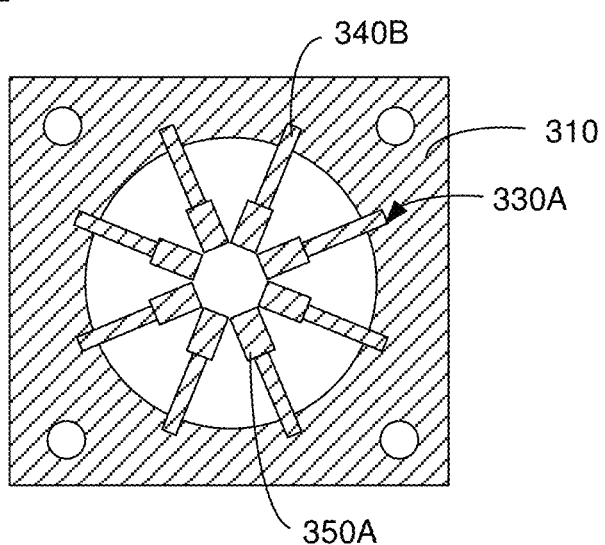

The support body 310A and 310B shown in FIG. 3A to FIG. 3H and the support body 210 shown in FIG. 2A to FIG. 2B have basically the same structure, and therefore, the similarity will be not further provided herein for brevity. The difference between them lies in that: when the fastening means are located at the contraction positions, the fastening means on several support units which are arranged side by side along the axial direction of the accommodation space form the first detector fastening ring together. In this specific embodiment, the fastening means 340A on the support body 310A are spaced by a certain distance which allows the arrangement of fastening means 340B on another support body 310B. When the support units 300A and 300B are arranged side by side along the axial direction, the fastening means 340A and 340B thereon are coupled to each other and form the first detector fastening ring. As shown in FIG. 3C to FIG. 3D, the detectors 350A and 350B respectively fixed to the fastening means 340A and 340B form a detection ring with a larger bore diameter. The support units 300A and 300B may have the same structure, and be only rotated by a certain angle relative to each other to couple the fastening means 340A and 340B, when building the emission tomography device. However, in the preferable embodiment shown in the drawings, two types of support units 300A and 300B can be provided, and the only difference therebetween is that the fastening means 340A and 340B are staggered by an angle.

Figure 3G:
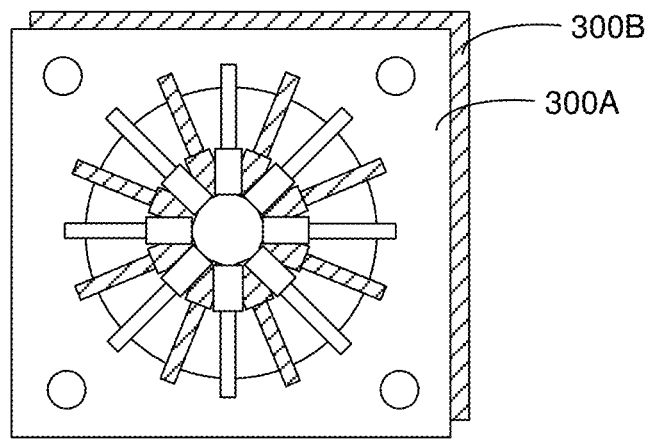
FIG. 3G to FIG. 3H are the front view and the side view of the assembled support units shown in FIG. 3E to FIG. 3F respectively, wherein the fastening means are located at extension positions.
Figure 3H:
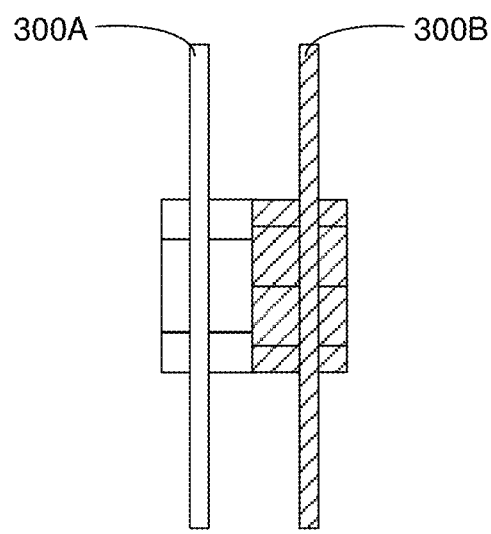

In order to reduce the bore diameter of the detection ring, as shown in FIG. 3E to FIG. 3H, the fastening means 340A and 340B could move to the extension positions along the radial direction respectively to form the second detector fastening ring of a second diameter. Thus, the detectors on the fastening means 340A form a detection ring of a smaller bore diameter, and the detectors on the fastening means 340B form another detection ring of a smaller bore diameter. The smaller bore diameter is about half of the bore diameter of the detection ring when both the fastening means 340A and 340B are located at contraction positions. In this case, when the support units 300A and 300B are arranged side by side along the axial direction, as shown in FIG. 3G to FIG. 3H, not only the bore diameter of the detection ring are decreased to half of the initial bore diameter, but also the axial length of the detection space are doubled compared with that when the fastening means 300A and 300B are located at contraction positions. As mentioned above, the detection sensitivity depends on the geometrical efficiency and the detection efficiency to the inherent coincidence event, and the geometrical efficiency depends on the space angle surrounded by the detector modules. Hence, when the bore diameter of the detection ring is decreased by half and the axial length of the detection ring doubles, the space angle is approximately increased to four times as compared with the initial space angle, which further improves the detection sensitivity of the emission tomography device by four times. It is more important that all of the detectors 350A and 350B on the support units 300A and 300B could be fully utilized.

The embodiment shown in FIG. 3A to FIG. 3H only illustrates the technical solution that the first detector fastening ring is formed by the fastening means from two support units. Nevertheless, the principle of the present invention could also be applied to the technical solution that the first detector fastening ring is formed by the fastening means from three or more support units. To be specific, the plurality of support positions on each support unit could be configured that the plurality of support positions on different support units are staggered and arranged alternately along the circumferential direction, when a predetermined number (for example, 2, 3 or more) of support units are arranged side by side along the axial direction of the accommodation space, so that the support positions on different support units could form the first detector fastening ring alternately. When all of the fastening means on each support unit move to the extension positions, the detection rings formed by them have a decreased bore diameter which is equal to ⅓, ¼, etc. of the initial bore diameter. Correspondingly, the detection sensitivity increases to 9, 16 . . . times.

Figure 4:
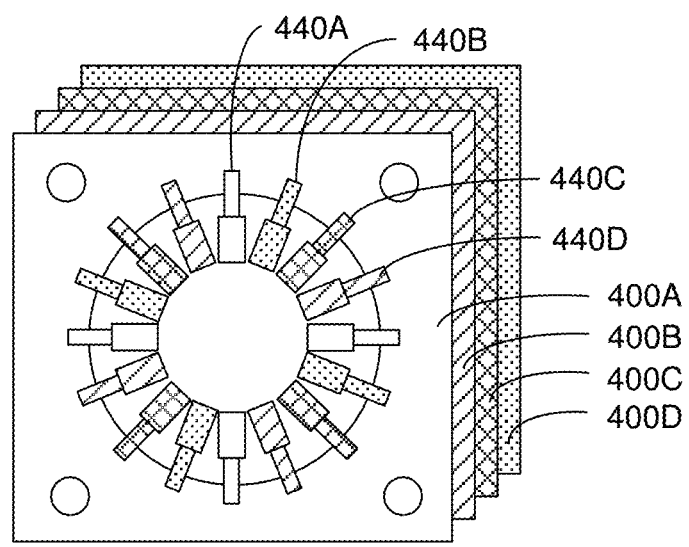
FIG. 4 schematically illustrates a support unit according to another embodiment of the present invention.

As shown in FIG. 4, it provides an embodiment that the fastening means 440A, 440B, 440C and 440D on the four support units 400A, 400B, 400C and 400D compose the first detector fastening ring. In this embodiment, the predetermined number is 4. The support positions for the fastening means 440A, 440B, 440C and 440D are staggered relative to each other along the circumferential direction, so that the fastening means 440A, 440B, 440C and 440D on the four support units are arranged alternately and form the first detector fastening ring. "Arranged alternately" means that in every cycle each of the fastening means 440A, 440B, 440C and 440D could present once. Nevertheless, the orders in which the fastening means 440A, 440B, 440C and 440D present in each cycle may be the same or not. Preferably, the support positions are configured to be arranged alternately in the same order when the predetermined number of the support units (e.g., 400A, 400B, 400C and 400D) are arranged side by side along the axial direction. That is, the support positions on the same support unit are the same or corresponding in each cycle. In the embodiment shown in FIG. 4, the fastening means are located in the order of 440A, 440B, 440C, 440D, 440A, 440B, 440C, 440D . . . .

Similarly, the four support units 400A, 400B, 400C and 400D may have the same structure, and only be rotated by different angles along the circumferential direction respectively when the emission tomography device is being built so that the fastening means could be staggered and arranged alternately. Alternatively, it is possible to provide four types of support units 400A, 400B, 400C and 400D. The difference between them lies in that the support positions of the fastening means 440A, 440B, 440C, 440D are staggered by a certain angle.

When all of the fastening means 440A, 440B, 440C, 440D on each of the support units 400A, 400B, 400C and 400D move to the extension positions, the formed detection rings have a decreased bore diameter which is equal to ¼ of the initial bore diameter. Additionally, along the axial direction, four detection rings have been formed, and thus the axial length is increased to 4 times of the original. Accordingly, the detection sensitivity could be improved to 16 times.

Figure 5A:
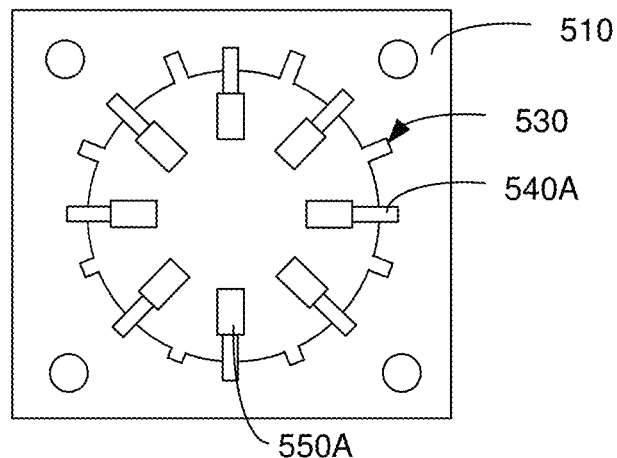
FIG. 5A to FIG. 5B schematically illustrate a support unit according to another embodiment of the present invention respectively.
Figure 5B:
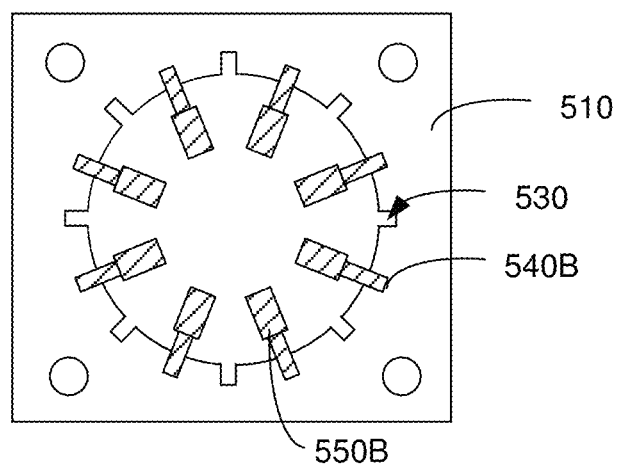

In another preferable embodiment, as shown in FIG. 5A to 5B, the fastening means 540A and 540B may be spaced apart. There is only one corresponding support position connected with a fastening means 540A or 540B for every predetermined number of support positions 530. In FIG. 5A, only one support position has a fastening means 540A for every two support positions 530. That is, every second support position has a fastening means 540A. In FIG. 5B, a similar arrangement is adopted. The difference lies in that: the fastening means 540A and 540B are complementary in positions, so that the fastening means 540A and 540B in their contraction positions could be arranged alternately and form the first detector fastening ring when the support units 500A and 500B are arranged side by side along the axial direction. Thus, the support bodies 510 of the support units 500A and 500B may be configured to have the same structure. The fastening means 540A and 540B may be fixed at different support positions 530 respectively as required. Therefore, there is no need to manufacture different types of support bodies 510 as mentioned in the above embodiment or rotate the support bodies 510 relative to each other when building the emission tomography device. Instead, the support body 510 and the fastening means may be manufactured in standard components and assembled as required when building the emission tomography device, which benefits the manufacturing, transportation, storage, and so on. It is noted that, in this embodiment, distinguishing the fastening means by A and B is for explicitly illustrating their difference in positions, and it is not necessary for the fastening means 540A and 540B to have the same of different structure or function.

Similarly, the principle of the embodiment may also be applied to the technical solution that the first detector fastening ring is formed by more than two support units. Although no drawings are provided to help describe the present invention, the person skilled in the art is able to apply the principle to the technical solution that the first detector fastening ring is formed by more than two support units after studying the disclosure above. In this case, the fastening means are spaced apart, so that there is only one corresponding support position connected with a fastening means to for every predetermined number of support positions. For example, there is only one support position connected with a fastening means for every three, four or more support positions. Preferably, the fastening means on the same support unit are located at the corresponding positions in each cycle. Thus, when the fastening means are located in extension positions, the fastening means on the same support unit could form a second detector fastening ring. As described above, when only one support position is connected with a fastening means for every three, the bore diameter of the second detection ring may be decreased to ⅓ of the initial bore diameter; Similarly, when only one support position connected with a fastening means for every four, the bore diameter of the second detection ring may be decreased to ¼ of the initial bore diameter; . . . . Correspondingly, when all of the fastening means on each support unit move to the extension positions, the axial length of the formed detection ring increases to 3, 4, . . . times of the original, and thus the detection sensitivity increases to 9, 16 . . . times.

Figure 6:
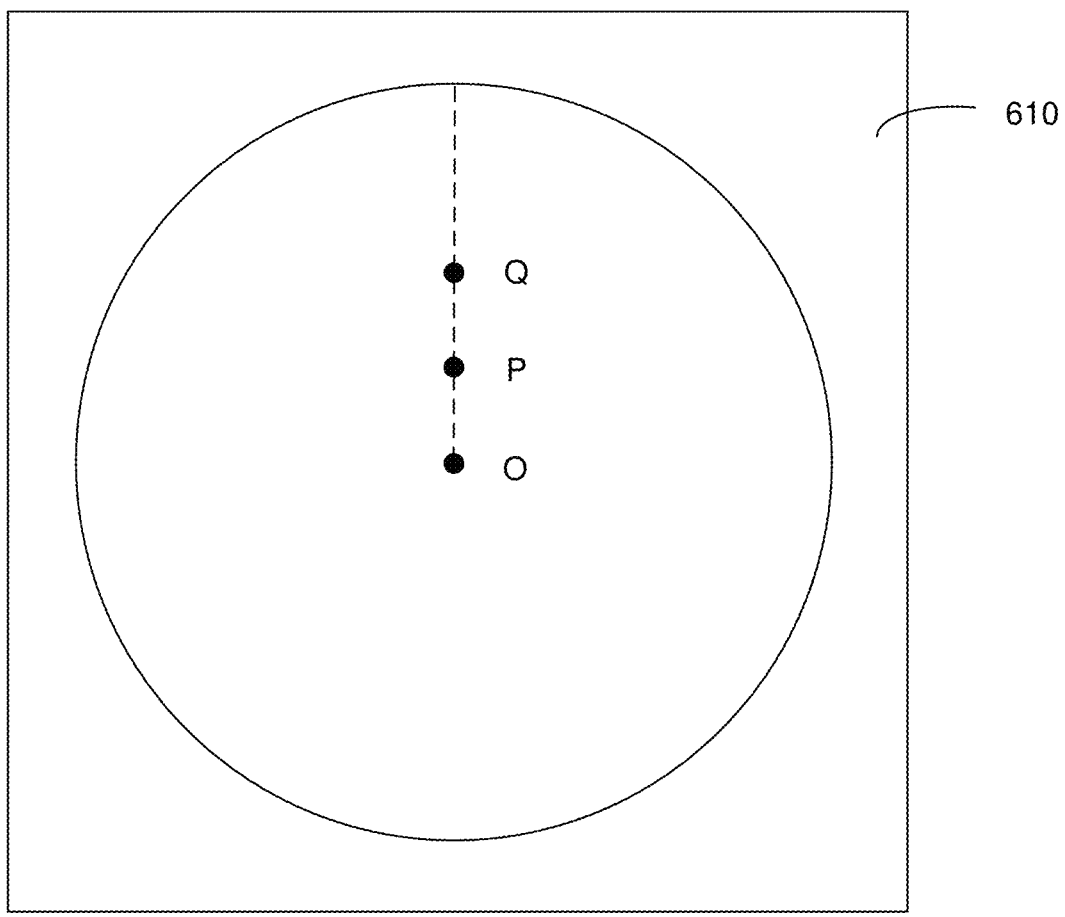
FIG. 6 is a simplified schematic view that schematically illustrates a support unit according to another embodiment of the present invention.

In every embodiment described above, the principle of the present invention is illustrated by the example of the technical solution that the fastening means has one extension position. Alternatively, the fastening means may also have a plurality of extension positions. The plurality of extension positions are arranged along the radial direction of a cylindrical bore. When the fastening means are located in extension positions, the second detector fastening ring may be formed by the fastening means on the same support body, or by the fastening means on the plurality of support units arranged side by side along the axial direction. For example, as shown in FIG. 6, the fastening means may have two extension positions, i.e., the first extension position P and the second extension position Q. The distance from the first extension position P to the center O of the accommodation space is less than the distance from the second extension position Q to the center O. For clarity, the fastening means and the detectors are omitted in FIG. 6. When the fastening means move to the first extension positions P, the detectors fixed thereon can form a complete detection ring. In this case, the fastening means on one support body 610 form a second detector fastening ring. When the fastening means move to the second extension position Q, a complete detection ring must be formed by the aid of the detectors fixed to the fastening means on the adjacent support units, since the distance from the second extension position Q to the center O is greater. In this case, the fastening means on the adjacent support bodies form the second detector fastening ring together. For reference to FIG. 2A, FIG. 3C and FIG. 4, the fastening means on the adjacent support bodies 610 together constituting the second detector fastening ring could be understand. Nevertheless, all the fastening means on the adjacent support bodies 610 are located at the second extension positions Q.

In one preferable embodiment, the number of the support units for forming the first detector fastening ring with the fastening means at contraction positions may be an composite number (which is not a prime number and can be divided exactly by other number in addition to itself and the number 1, e.g., 4, 6, 8, 9, 10, etc.), so as to form a relatively complex system with multiple extension positions. In this case, the number of the extension positions may be u, wherein u is the number of the prime factors of the composite number except 1. The u extension positions are arranged along the radial direction of the accommodation space. The distances from the u extension positions to the center of the accommodation space are respectively equal to the product of the reciprocal of each of the u prime factors and r, wherein r is the distance from the fastening means at contraction position to the center of the accommodation space.

For example, in the technical solution that the first detector fastening ring is formed by 6 support units, since the composite number 6 has prime factors 1, 6, 2 and 3, the u prime factors include 2, 3 and 6 and thus u=3. The distances from these 3 extension positions to the center of the accommodation space is r/2, r/3 and r/6 respectively.

In the embodiments similar to that shown in FIG. 5A to FIG. 5B, for every 6 support positions, there is only one corresponding position connected with the fastening means. Thus, the first detector fastening ring may be formed by 6 support units. These 6 support units include: a support unit 1, connected with a fastening means at the first position of every 6 support positions; a support unit 2, connected with a fastening means at the second position of every 6 support positions; a support unit 3, connected with a fastening means at the third position of every 6 support positions; a support unit 4, connected with a fastening means at the fourth position of every 6 support positions; a support unit 5, connected with a fastening means at the fifth position of every 6 support positions; and a support unit 6, connected with a fastening means at the sixth position of every 6 support positions. When the fastening means are all at contraction positions, the first to sixth support units could form the first detector fastening ring together. In the present embodiment, three second detector fastening rings could be formed in total. Specifically, when the fastening means on each of the support units are at the first extension position (which is closest to the center), they form a second detector fastening ring, wherein the distance from the first extension position to the center of the accommodation space is about equal to r/6. When the fastening means on each of the support units are at the second extension position (which is further away from the center than the first extension position), they form another second detector fastening ring, wherein every two support units (i.e., the support units 1 and 4, the support units 2 and 5, and the support units 3 and 6) could form such a second detector fastening ring respectively. The distance from the second extension position to the center of the accommodation space is equal to r/3. When the fastening means on each of the support units are at the third extension position (which is further away from the center than the second extension position), they form yet another second detector fastening ring, wherein every three support units (i.e., the support units 1, 3 and 5, the support units 2, 4 and 6) could form such a second detector fastening ring respectively. The distance from the third extension position to the accommodation space is equal to r/2, and two such second detector fastening rings can are formed in total by six support units.

It is noted that, the distances r in various directions of the support units do not have to be completely equal to each other. For example, in the embodiment that the accommodation space is in shape of an elliptic cylinder, the distance from the extension position to the center decreases to a fraction of r refers to the relation between the extension position and the fixed position in the same radial direction, rather than a position relation in different radial directions.

Although the disclosure above explains the principle of the complex system with multiple extension positions by taking example of the technical solution that every predetermined number of support positions is provided with one fastening means, the principle of the complex system with multiple extension positions could also be applied to the embodiment (e.g., as shown in FIG. 3A to FIG. 3H) that the support units are the same and the fastening means on the different support units couple with each other by rotating the support units by a certain angle. For example, when the first detector fastening ring is formed by 6 support units, 2, 3 or 6 support units could be rotated by different angle to form different second detector fastening rings, respectively. No more detail will be described herein.

The principle of the complex system with multiple extension positions are explained by the example that the first detector fastening ring is formed by 6 support units, but the person skilled in the art could extend the composite number from 6 to others after studying the present disclosure.

Obviously, when the complex system with multiple extension positions changes the radial size of the second detector fastening ring, there is a need to rotate the support units and alter the distance between the adjacent support units, or to adjust the position relation between the adjacent support units. For example, in the above embodiment, when three second detector fastening rings respectively composed of the support units 1 and 4, the support units 2 and 5, and the support units 3 and 6 are changed to two second detector fastening rings respectively composed of the support units 1, 3 and 5, and the support units 2, 4 and 6, the position relation between the support units is adjusted until the support units for constituting the same second detector fastening ring are adjacent to each other. However, the advantages of such an arrangement cannot be ignored, since the radial size of the second detector fastening ring could be adjusted as required and thus the system has more adjustable value. Obviously, in other embodiment, their position relation may also be unchanged, which, however, would cause the detectors on part of the support ring in an invalid state.

In further preferable embodiments, the number of the support units constituting the first detector fastening rings with the fastening means at contraction positions may be set to $2^n$, wherein n is an integer greater than or equal to 2. In this case, the number of the extension positions may be n, and n extension positions are arranged along the radial direction of the accommodation space. The distances from the n extension positions to the center of the accommodation space are equal to $r/2, r/4, \ldots r/2^n$, respectively, wherein r is the distance from the fastening means at contraction position to the center of the accommodation space. For example, in the embodiment that n=2, i.e., the number of the extension positions is 2, as shown in FIG. 6, the first detector fastening ring could be formed by four support units when the fastening means are located at contraction positions. The distance from the first extension position P to the center O may be r/4, and the distance from the second extension position Q to the center O is may be r/2. When the fastening means move to the first extension positions P, the fastening means on the same support unit could form the second detector fastening ring. When the fastening means move to the second extension positions Q, the fastening means on two adjacent support units could form the second detector fastening ring. Thus, after the emission tomography device is built, the second detector fastening rings with various radial sizes could be formed simply by varying the axial distances between the support units, which is relatively easier as compared with rebuilding a system. However, there is some limitation on the obtainable radial size of the second detector fastening ring.

Similarly, n may also be equal to 3, 4, 5 . . . . According to the above disclosure, the skilled in the art could deduce the specific arrangement of the embodiments that n=3, 4, 5 . . . , which will not be described in more detail for brevity.

It is noted that, in various embodiments above, the number of the fastening means on each support unit for fixing the detectors is preferably more than one. The person skilled in the art could understand, when the fastening means on each support unit form the second detector fastening ring by themselves, for example, in PET device, a pair of gamma photons should be detected in opposite directions simultaneously. Therefore, the number of the fastening means on each support unit is at least 2. Therefore, the person skilled in the art could realize to arrange more than two fastening means on each support unit when building the PET device though the support unit according to the present invention.

In one preferable embodiment, the support bodies, for example, 210, 310A, 310B, 410, 510 and 610, may have a rectangular plate-structure. The support body may be manufactured by an aluminum plate or steel plate. The rectangular shape is easy to manufacture, and for the support unit to be positioned according to a predetermined orientation. The plate structure could reduce the materials consumption, decrease the weight and facilitate transportation, and avoid blocking the movement of the support units when the plurality of support units are arranged side by side along the axial direction, such that the support units are movable in a relatively wide axial range.

The support units may be moved axially by manual or through an auxiliary mechanical tool. When the auxiliary mechanical tool is adopted, preferably, the support body is provided with guide holes, for example the guide holes 260 as shown in FIG. 2A to FIG. 2B, for guiding the support unit to move along the axial direction of the accommodation space.

In another aspect, the present invention provides a support device for the emission tomography device. Back to FIG. 1, the support device includes a plurality of support units 111, 112, 113 and 114. The plurality of support units 111, 112, 113 and 114 may be anyone or more types of the support units mentioned above. The plurality of support units 111, 112, 113 and 114 are arranged along the axial direction of the accommodation space, and the accommodation space form an accommodation chamber for accommodating the detectors and the detected object. The detectors are fixed to the fastening means on the support units 111, 112, 113 and 114 in the accommodation space. The space surrounded by the detectors serves as the detection chamber for accommodating the detected object. According to the description above, since the fastening means are movable in the radial directions, the bore diameter of the detection chamber is adjustable. Thus, the emission tomography device is suitable for detected objects with various sizes. The components included in the support unit could be described with reference to the disclosure above, and there is no need to repeat them herein.

Additionally, the support device 100 also includes a guide means 120 for moving the plurality of support units 111, 112, 113 and 114 along the axial direction of the accommodation space. Additionally, to some extent, the guide means 120 could serve to position the plurality of support units 111, 112, 113 and 114 along the axial direction of the accommodation space.

In one preferable embodiment, the guide means 120 comprises guide rails 121 arranged along the axial direction of the accommodation space and guide holes 122 provided on the support bodies of the support units 111, 112, 113 and 114. The guide rails 121 pass through the guide holes 122 so as to guide the support units 111, 112, 113 and 114 to move along the guide rails 121. The guide holes 122 are substantially the same as the guide holes 260 described above. More preferably, as to the support body having a rectangular plate-structure, the guide means 120 comprises four guide rails 121 and four guide holes 122 arranged in the four corners of each of the support bodies, so as to guide the support units 111, 112, 113 and 114 to move along the guide rails 121 smoothly.

In another preferable embodiment, the support device 100 further comprises elastic buffer means 130 arranged between the adjacent support units. The elastic buffer means 130 is used to apply equivalent elastic force to the support units on its two sides. Thus, uneven stress is avoided and the distance between the support units is adjustable. Additionally, the support units 111, 112, 113 and 114 could be prevented from being damaged by excessive force while they are moved. For example, the elastic buffer means 130 may be a compressible cylinder, a spring, a sponge, compressible polymer materials or compressible rubber, etc. Additionally, the support device 100 further includes a positioning device (not shown) for positioning the support units 111, 112, 113 and 114 in the axial direction of the accommodation space. The positioning device may be various kinds of positioning device known in the art, for example, positioning bolt, etc.

According to another aspect of the present invention, an emission tomography device is further provided. The emission tomography device may comprise any support device 100 as described above and detectors. The detector may be fixed to the fastening means of the support device 100 in the accommodation chamber.

Figure 7:
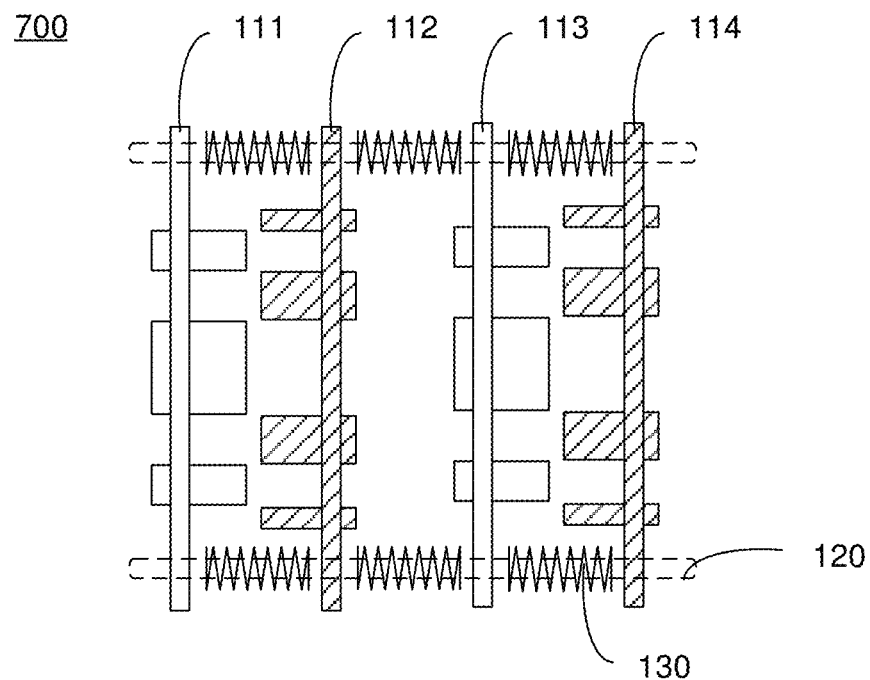
FIG. 7 is a side view of the support device according to an embodiment of the present invention, wherein the fastening means are uncoupled thereto and located at contraction positions.
Figure 8A:
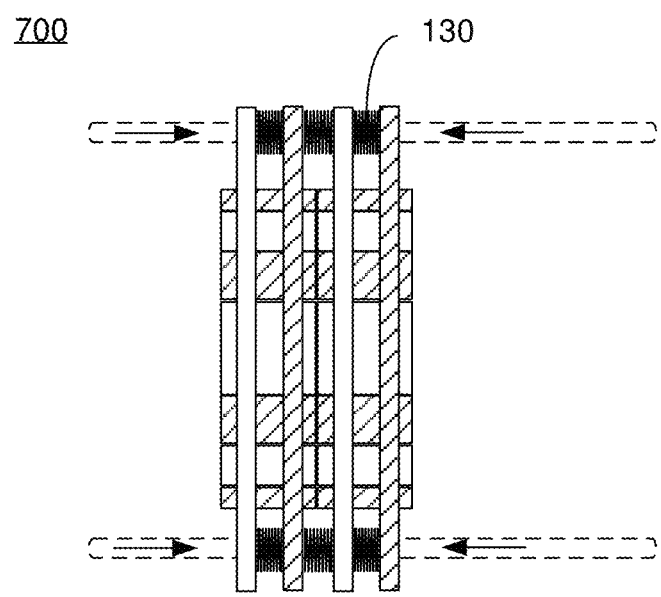
FIG. 8A to FIG. 8B are side and the front views of the support device according to an embodiment of the present invention, wherein the fastening means are coupled thereto and located at contraction positions.
Figure 8B:
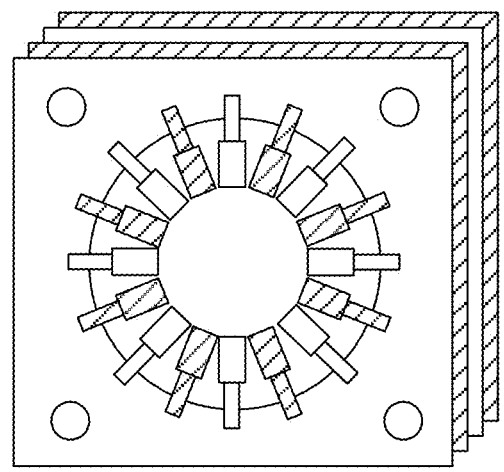

Now, a preferable method for adjusting the emission tomography device is illustrated by the example of the support device having adjustable radial and axial lengths. As shown in FIG. 7 to FIG. 11, the fastening means on every two support units 111-112 and 113-114 could form a first detector fastening ring. The drawings show that there are two first detector fastening rings. Obviously, more or less support units could be arranged as required. When a detection chamber with relatively larger bore diameter is required, the support units 111, 112, 113 and 114 and the elastic buffer means 130 are firstly assembled together through the guide means 120, as shown in FIG. 7. In the case that the guide means includes the guide rail 120 and the guide hole and the elastic buffer means 130 is a spring, the guide rail 120 could pass through the elastic buffer means 130 and the guide holes of the support units. The fastening means may move to the contraction position before or after the support units are fixed to the guide means 120. Similarly, the detector may be fixed to the fastening means before or after the fastening means moves to the contraction position. Then, force applies on the support device from both sides, so that the fastening means on the support units 111 and 112 are coupled, and the fastening means on the support units 113 and 114 are coupled. Besides, the detectors could abut to each other, as shown in FIG. 8A to FIG. 8B. The elastic buffer means 130 is compressed. Thus, a detection chamber with a relatively larger bore diameter is formed.

Figure 9:
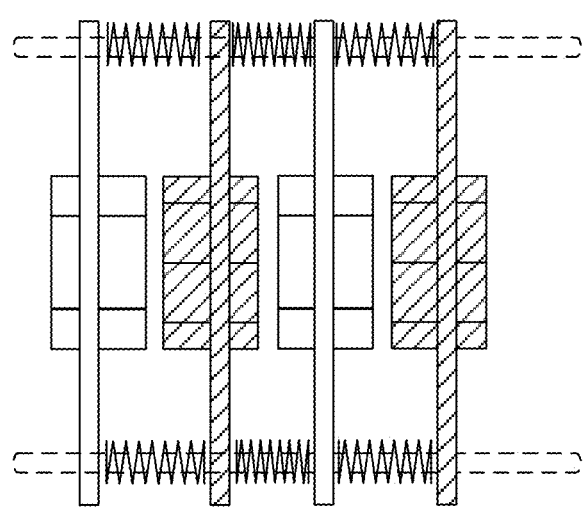
FIG. 9 is a side view of the support device according to an embodiment of the present invention, wherein the fastening means are uncoupled thereto and located at extension positions.
Figure 10A:
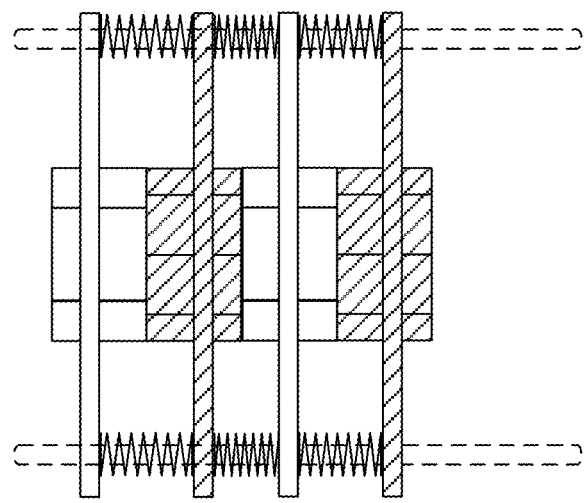
FIG. 10A to FIG. 10B are side and front views of the support device according to an embodiment of the present invention, wherein the fastening means are coupled thereto and located at extension positions.
Figure 10B:
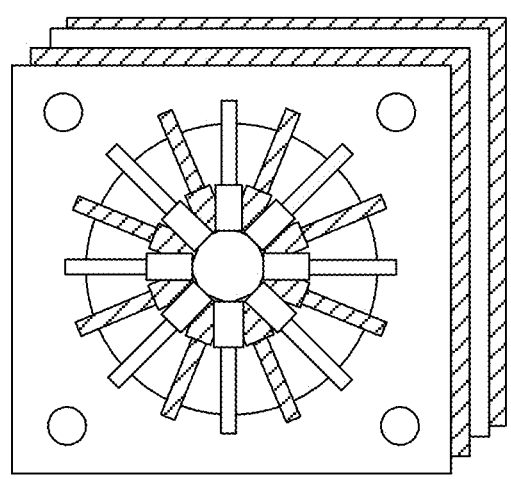

When a detection chamber with a relatively smaller bore diameter is needed, the force applied to the emission tomography device of FIG. 8A to FIG. 8B is removed so as to separate the adjacent support units, and then the fastening means on each of the support units 111, 112, 113 and 114 move to the extension positions to form the second detection chamber, as shown in FIG. 9. Finally, force applies on the support device from both sides again, until the adjacent detectors on the second detector fastening ring abut to each other, as shown in FIG. 10A to FIG. 10B. Thus, a detection chamber with a relatively small bore diameter is formed.

In the emission tomography device built by the support units provided by the present invention, at least the radial length of its detection chamber is adjustable. Thus, a detection chamber with a relative larger bore diameter could be form as required, for example, for an adult, and a detection chamber with a relative smaller bore diameter could be formed as required, for example, for a child or a small animal. Therefore, a relative larger space angle could be obtained as compared with the emission tomography device in the prior art, and thus the detection sensitivity of the emission tomography device is improved effectively.

The present invention is disclosed by describing the embodiments above. However, it should be understood that the embodiments above are for example and illustrative purpose only, rather than limit the present invention to the scope of the embodiments described above. The person skilled in the art could understand that the present invention is not limited to the above embodiments, and more variations and modifications, falling into the protection scope claimed by the present invention, could be made according to the teaching of the present invention. The protection scope of the present invention is defined by the appended claims and their equivalent scope.

The invention claimed is:

1. A support unit for an emission tomography device, characterized in that it comprises:
    a support body, provided with an accommodation space running through the support body therein, wherein the support body comprises a plurality of support positions that are distributed along a circumferential direction of the accommodation space;
    a plurality of fastening means, connected to at least a portion of the plurality of support positions, for fixing detectors of the emission tomography device, wherein at least a portion of the plurality of fastening means are movable between contraction positions and extension positions along radial directions of the accommodation space,
    wherein the fastening means are used for forming a first detector fastening ring with a first diameter when at the contraction positions and forming a second detector fastening ring with a second diameter which is smaller than the first diameter when at the extension positions,
    wherein the plurality of support positions are configured that when a predetermined number of the support units are arranged side by side along the axial direction of the accommodation space, support positions on different support units are staggered and arranged alternately along the circumferential direction, in order for the fastening means on the predetermined number of the support units to form the first detector fastening ring alternately.

2. The support unit of claim 1, characterized in that: when the fastening means are at the contraction positions, the fastening means on a plurality of the support units arranged side by side along the axial direction of the accommodation space are capable of forming the first detector fastening ring together.

3. The support unit of claim 1, characterized in that: when the fastening means are at the extension positions, the fastening means on the same support body are capable of forming the second detector fastening ring; or the fastening means on a plurality of the support units arranged side by side along the axial direction of the accommodation space are capable of forming the second detector fastening ring together.

4. The support unit of claim 1, characterized in that: the plurality of the support positions are configured that when the predetermined number of the support units are arranged side by side along the axial direction, support positions on different support units are staggered and arranged alternately in the same order.

5. The support unit of claim 1, characterized in that: the predetermined number is a composite number, the number of the extension positions is u, wherein u is the number of the prime factors of the composite number except 1, the u extension positions are arranged along the radial directions of the accommodation space and the distances from the u extension positions to the center of the accommodation space are respectively equal to the product of the reciprocal of each of the u prime factors and r, wherein r is the distance from the fastening means at the contraction position to the center of the accommodation space.

6. The support unit of claim 5, characterized in that: the predetermined number is $2^n$, wherein n is an integer greater than or equal to 2; and the number of the extension positions is n, and the distance from the n extension positions to the center of the accommodation space are equal to $r/2$, $r/4$, . . . $r/2n$, respectively.

7. The support unit of claim 1, characterized in that: the support body has a rectangular plate-structure.

8. The support unit of claim 1, characterized in that: the support body is provided with guide holes, for guiding the support unit to move along the axial direction of the accommodation space.

9. A support device for an emission tomography device, characterized in that it comprises:
    a plurality of support units, wherein the plurality of support units are arranged side by side along the axial direction of the accommodation space, and the accommodation space forms an accommodation chamber for accommodating detectors and a detected object, each of the plurality of support units comprising:
    a support body, provided with an accommodation space running through the support body therein, wherein the support body comprises a plurality of support positions that are distributed along a circumferential direction of the accommodation space;
    a plurality of fastening means, connected to at least a portion of the plurality of support positions, for fixing detectors of the emission tomography device, wherein at least a portion of the plurality of fastening means are movable between contraction positions and extension positions along radial directions of the accommodation space, wherein the fastening means are used for forming a first detector fastening ring with a first diameter when at the contraction positions and forming a second detector fastening ring with a second diameter which is smaller than the first diameter when at the extension positions, wherein the plurality of support positions are configured that when a predetermined number of the support units are arranged side by side along the axial direction of the accommodation space, support positions on different support units are staggered and arranged alternately along the circumferential direction, in order for the fastening means on the predetermined number of the support units to form the first detector fastening ring alternately.

10. The support device of claim 9, characterized in that: the support device further comprises a guide means, for moving the plurality of the support units along the axial direction of the accommodation space.

11. The support device of claim 10, characterized in that: the guide means includes a guide rail arranged along the axial direction of the accommodation space and guide holes arranged on the support bodies, and the guide rail passes through the guide holes to guide the support units to move along the guide rail.

12. The support device of claim 11, characterized in that: when the support body has a rectangular plate-structure, the guide means comprises four guide rails and four guide holes arranged at four corners of each of the support bodies.

13. The support device of claim 10, characterized in that the support device further comprises:
an elastic buffer means, arranged between the adjacent support units to apply equivalent elastic force to the support units on two sides of the elastic buffer means; and
a positioning device, for positioning the support units in the axial direction of the accommodation space.

14. The support device of claim 9, characterized in that: when the fastening means are at the contraction positions, the fastening means on a plurality of the support units arranged side by side along the axial direction of the accommodation space are capable of forming the first detector fastening ring together.

15. The support device of claim 9, characterized in that: when the fastening means are at the extension positions, the fastening means on the same support body are capable of forming the second detector fastening ring; or the fastening means on a plurality of support units arranged side by side along the axial direction of the accommodation space are capable of forming the second detector fastening ring together.

16. The support device of claim 9, characterized in that: the plurality of the support positions are configured that when the predetermined number of the support units are arranged side by side along the axial direction, support positions on different support units are staggered and arranged alternately in the same order.

17. The support device of claim 9, characterized in that: the predetermined number is a composite number, the number of the extension positions is u, wherein u is the number of the prime factors of the composite number except 1, the u extension positions are arranged along the radial directions of the accommodation space and the distances from the u extension positions to the center of the accommodation space are respectively equal to the product of the reciprocal of each of the u prime factors and r, wherein r is the distance from the fastening means at the contraction position to the center of the accommodation space.

18. The support device of claim 17, characterized in that: the predetermined number is $2^n$, wherein n is an integer greater than or equal to 2; and the number of the extension positions is n, and the distance from the n extension positions to the center of the accommodation space are equal to $r/2, r/4, \ldots r/2n$, respectively.

19. An emission tomography device, characterized in that it comprises:
a support device, comprising a plurality of support units, wherein the plurality of support units are arranged side by side along the axial direction of the accommodation space, and the accommodation space forms an accommodation chamber for accommodating detectors and a detected object; and
a detector, fixed to the fastening means within the accommodation chamber,
wherein each of the plurality of support units comprises:
a support body, provided with an accommodation space running through the support body therein, wherein the support body comprises a plurality of support positions that are distributed along a circumferential direction of the accommodation space;
a plurality of fastening means, connected to at least a portion of the plurality of support positions, for fixing detectors of the emission tomography device, wherein at least a portion of the plurality of fastening means are movable between contraction positions and extension positions along radial directions of the accommodation space,
wherein the fastening means are used for forming a first detector fastening ring with a first diameter when at the contraction positions and forming a second detector fastening ring with a second diameter which is smaller than the first diameter when at the extension positions,
wherein the plurality of support positions are configured that when a predetermined number of the support units are arranged side by side along the axial direction of the accommodation space, support positions on different support units are staggered and arranged alternately along the circumferential direction, in order for the fastening means on the predetermined number of the support units to form the first detector fastening ring alternately.

* * * * *